United States Patent
Ghosh et al.

(10) Patent No.: US 10,004,906 B2
(45) Date of Patent: Jun. 26, 2018

(54) CONFIRMING SENSED ATRIAL EVENTS FOR PACING DURING RESYNCHRONIZATION THERAPY IN A CARDIAC MEDICAL DEVICE AND MEDICAL DEVICE SYSTEM

(71) Applicant: Medtronic, Inc., Minneapolis, MN (US)

(72) Inventors: Subham Ghosh, Blaine, MN (US); Juan Du, Minneapolis, MN (US); Saul E Greenhut, Aurora, CO (US); Michael T Hemming, Kiowa, CO (US)

(73) Assignee: Medtronic, Inc., Minneapolis, MN (US)

( * ) Notice: Subject to any disclaimer, the term of this patent is extended or adjusted under 35 U.S.C. 154(b) by 0 days. days.

(21) Appl. No.: 14/801,049

(22) Filed: Jul. 16, 2015

(65) Prior Publication Data

US 2017/0014629 A1    Jan. 19, 2017

(51) Int. Cl.
*A61B 5/00* (2006.01)
*A61N 1/368* (2006.01)
(Continued)

(52) U.S. Cl.
CPC .......... *A61N 1/3682* (2013.01); *A61B 5/0422* (2013.01); *A61B 5/0452* (2013.01);
(Continued)

(58) Field of Classification Search
CPC . A61B 5/0245; A61B 5/04012; A61B 5/0402; A61B 5/0452; A61B 5/04525;
(Continued)

(56) References Cited

U.S. PATENT DOCUMENTS

| 4,374,382 A | 2/1983 | Markowitz |
|---|---|---|
| 4,428,378 A | 1/1984 | Anderson et al. |

(Continued)

FOREIGN PATENT DOCUMENTS

| EP | 0 597 728 A2 | 5/1994 |
|---|---|---|
| EP | 0 726 082 A2 | 8/1996 |

(Continued)

OTHER PUBLICATIONS

U.S. Appl. No. 13/665,601 to Bonner et al., entitled, "Leadless Pacemaker System," filed Oct. 31, 2012.
(Continued)

*Primary Examiner* — Eugene T Wu

(57) ABSTRACT

A medical device and medical device system for controlling delivery of therapeutic stimulation pulses that includes a sensing device to sense a cardiac signal and emit a trigger signal in response to the sensed cardiac signal, a therapy delivery device to receive the trigger signal and deliver therapy to the patient in response to the emitted trigger signal, and a processor positioned within the sensing device, the processor configured to determine whether the sensed cardiac signal exceeds a possible P-wave threshold, compare a portion of the sensed cardiac signal to a P-wave template having a sensing window having a length less than a width of the P-wave, confirm an occurrence of a P-wave signal in response to the comparing, emit the trigger signal in response to the occurrence of a P-wave signal being confirmed, and inhibit delivery of the emitting signal in response to the occurrence of a P-wave signal not being confirmed.

37 Claims, 7 Drawing Sheets

(51) Int. Cl.
*A61B 5/0452* (2006.01)
*A61N 1/375* (2006.01)
*A61N 1/365* (2006.01)
*A61B 5/042* (2006.01)
*A61N 1/362* (2006.01)

(52) U.S. Cl.
CPC ........ *A61B 5/04525* (2013.01); *A61B 5/7246* (2013.01); *A61B 5/7285* (2013.01); *A61N 1/36507* (2013.01); *A61N 1/3756* (2013.01); *A61N 1/3627* (2013.01)

(58) Field of Classification Search
CPC ... A61B 5/7221; A61B 5/7235; A61B 5/7246; A61B 5/7271; A61B 5/7282; A61B 5/7285; A61B 5/7292; A61N 1/0504; A61N 1/368; A61N 1/3682; A61N 1/3684; A61N 1/365; A61N 1/37; A61N 1/3702; A61N 1/3704; A61N 1/37205; A61N 1/3756
See application file for complete search history.

(56) References Cited

U.S. PATENT DOCUMENTS

| | | | |
|---|---|---|---|
| 4,481,950 A | 11/1984 | Duggan | |
| 4,543,955 A | 10/1985 | Schroeppel | |
| 4,787,389 A | 11/1988 | Tarjan | |
| 5,052,388 A | 10/1991 | Sivula et al. | |
| 5,113,859 A | 5/1992 | Funke | |
| 5,117,824 A | 6/1992 | Keimel et al. | |
| 5,179,949 A | 1/1993 | Chirife | |
| 5,312,445 A * | 5/1994 | Nappholz | A61N 1/365 607/9 |
| 5,354,316 A | 10/1994 | Keimel | |
| 5,374,280 A | 12/1994 | Den Dulk | |
| 5,402,070 A | 3/1995 | Shelton et al. | |
| 5,411,535 A | 5/1995 | Fujii et al. | |
| 5,507,782 A | 5/1996 | Kieval | |
| 5,545,186 A | 8/1996 | Olson et al. | |
| 5,620,474 A | 4/1997 | Koopman | |
| 5,683,432 A | 11/1997 | Goedeke | |
| 5,690,689 A | 11/1997 | Sholder | |
| 5,690,691 A | 11/1997 | Chen et al. | |
| 5,741,308 A | 4/1998 | Sholder | |
| 5,755,739 A | 5/1998 | Sun et al. | |
| 5,794,624 A * | 8/1998 | Kwong | A61B 5/04525 600/515 |
| 5,814,089 A | 9/1998 | Stokes et al. | |
| 5,855,593 A | 1/1999 | Olson et al. | |
| 5,893,882 A | 4/1999 | Peterson et al. | |
| 5,902,326 A | 5/1999 | Lessar et al. | |
| 5,954,649 A | 9/1999 | Chia et al. | |
| 6,016,448 A | 1/2000 | Busacker et al. | |
| 6,108,579 A | 8/2000 | Snell et al. | |
| 6,167,307 A | 12/2000 | Hess | |
| 6,206,847 B1 | 3/2001 | Edwards et al. | |
| 6,208,894 B1 | 3/2001 | Schulman et al. | |
| 6,263,242 B1 | 7/2001 | Mika et al. | |
| 6,292,693 B1 | 9/2001 | Darvish et al. | |
| 6,298,261 B1 | 10/2001 | Rex | |
| 6,324,427 B1 | 11/2001 | Florio | |
| 6,393,316 B1 | 5/2002 | Gillberg et al. | |
| 6,477,415 B1 | 11/2002 | Yerich | |
| 6,477,420 B1 | 11/2002 | Struble et al. | |
| 6,508,771 B1 | 1/2003 | Padmanabhan et al. | |
| 6,522,915 B1 | 2/2003 | Ceballos et al. | |
| 6,592,519 B1 | 7/2003 | Martinez | |
| 6,622,046 B2 | 9/2003 | Fraley et al. | |
| 6,628,989 B1 | 9/2003 | Penner et al. | |
| 6,738,668 B1 | 5/2004 | Mouchawar et al. | |
| 6,754,528 B2 | 6/2004 | Bardy et al. | |
| 6,764,446 B2 | 7/2004 | Wolinsky et al. | |
| 6,772,005 B2 | 8/2004 | Casavant | |
| 6,876,881 B2 | 4/2005 | Baumann et al. | |
| 6,904,315 B2 | 6/2005 | Panken et al. | |
| 6,931,279 B2 | 8/2005 | Ousdigian et al. | |
| 6,948,950 B2 | 9/2005 | Yamaguchi | |
| 7,024,248 B2 | 4/2006 | Penner et al. | |
| 7,031,772 B2 | 4/2006 | Condie | |
| 7,079,895 B2 | 7/2006 | Verbeek et al. | |
| 7,149,577 B2 | 12/2006 | Sharma | |
| 7,181,284 B2 | 2/2007 | Burnes et al. | |
| 7,198,603 B2 | 4/2007 | Penner et al. | |
| 7,209,790 B2 | 4/2007 | Thompson et al. | |
| 7,218,965 B2 | 5/2007 | Casavant | |
| 7,248,924 B2 | 7/2007 | Casavant | |
| 7,254,442 B2 | 8/2007 | Van Gelder et al. | |
| 7,283,874 B2 | 10/2007 | Penner | |
| 7,505,813 B1 | 3/2009 | Gill et al. | |
| 7,515,960 B2 | 4/2009 | Sharma | |
| 7,532,929 B2 | 5/2009 | Mussig et al. | |
| 7,558,631 B2 | 7/2009 | Cowan et al. | |
| 7,606,621 B2 | 10/2009 | Brisken et al. | |
| 7,610,092 B2 | 10/2009 | Cowan et al. | |
| 7,623,911 B2 | 11/2009 | Sarkar | |
| 7,634,313 B1 | 12/2009 | Kroll et al. | |
| 7,689,279 B2 | 3/2010 | Ziegler | |
| 7,702,390 B1 | 4/2010 | Min | |
| 7,706,879 B2 | 4/2010 | Burnes et al. | |
| 7,711,421 B2 | 5/2010 | Shafer et al. | |
| 7,742,812 B2 | 6/2010 | Ghanem et al. | |
| 7,869,876 B2 | 1/2011 | Prakash | |
| 7,881,791 B2 | 2/2011 | Sambelashvili et al. | |
| 7,904,153 B2 | 3/2011 | Greenhut et al. | |
| 7,925,343 B1 | 4/2011 | Min et al. | |
| 7,930,027 B2 | 4/2011 | Prakash et al. | |
| 7,930,031 B2 | 4/2011 | Penner | |
| 7,941,218 B2 | 5/2011 | Sambelashvili et al. | |
| 7,945,064 B2 | 5/2011 | O'Brien, Jr. et al. | |
| 7,991,467 B2 | 8/2011 | Markowitz et al. | |
| 8,145,308 B2 | 3/2012 | Sambelashvili et al. | |
| 8,160,684 B2 | 4/2012 | Ghanem et al. | |
| 8,170,666 B2 | 5/2012 | Sheldon | |
| 8,204,590 B2 | 6/2012 | Sambelashvili et al. | |
| 8,214,041 B2 | 7/2012 | Van Gelder et al. | |
| 8,233,980 B2 | 7/2012 | Pei | |
| 8,275,432 B2 | 9/2012 | Kuhn et al. | |
| 8,352,025 B2 | 1/2013 | Jacobson | |
| 8,364,276 B2 | 1/2013 | Willis | |
| 8,391,964 B2 | 3/2013 | Musley et al. | |
| 8,401,629 B2 | 3/2013 | Stadler | |
| 8,428,716 B2 | 4/2013 | Mullen et al. | |
| 8,433,409 B2 | 4/2013 | Johnson et al. | |
| 8,452,402 B2 | 5/2013 | Ecker et al. | |
| 8,457,742 B2 | 7/2013 | Jacobson | |
| 8,521,268 B2 | 8/2013 | Zhang et al. | |
| 8,532,785 B1 | 9/2013 | Crutchfield et al. | |
| 8,540,631 B2 | 9/2013 | Penner et al. | |
| 8,541,131 B2 | 9/2013 | Lund et al. | |
| 8,617,082 B2 | 12/2013 | Zhang et al. | |
| 8,639,333 B2 | 1/2014 | Stadler et al. | |
| 8,652,048 B2 | 2/2014 | Skerl et al. | |
| 8,666,505 B2 | 3/2014 | O'Brien et al. | |
| 8,744,572 B1 | 6/2014 | Greenhut et al. | |
| 8,768,459 B2 | 7/2014 | Ghosh et al. | |
| 8,798,745 B2 | 8/2014 | Jacobson | |
| 8,886,307 B2 | 11/2014 | Sambelashvili et al. | |
| 8,923,963 B2 | 12/2014 | Bonner et al. | |
| 9,566,013 B2 * | 2/2017 | Sambelashvili | A61B 5/04012 |
| 2004/0147966 A1 | 7/2004 | Ding et al. | |
| 2004/0186523 A1 | 9/2004 | Florio | |
| 2004/0193223 A1 | 9/2004 | Kramer et al. | |
| 2004/0215254 A1 | 10/2004 | Boute et al. | |
| 2004/0215262 A1 | 10/2004 | Ferek-Petric | |
| 2004/0230243 A1 | 11/2004 | Haefner et al. | |
| 2005/0027321 A1 | 2/2005 | Ferek-Petric | |
| 2005/0131480 A1 | 6/2005 | Kramer et al. | |
| 2005/0209648 A1 | 9/2005 | Burnes et al. | |
| 2006/0047319 A1 | 3/2006 | Bruhns et al. | |
| 2006/0116592 A1 | 6/2006 | Zhou et al. | |
| 2006/0116595 A1 * | 6/2006 | Palreddy | A61B 5/04525 600/516 |

(56) References Cited

U.S. PATENT DOCUMENTS

| | | |
|---|---|---|
| 2006/0116596 A1 | 6/2006 | Zhou et al. |
| 2006/0235478 A1 | 10/2006 | Van Gelder et al. |
| 2007/0129762 A1 | 6/2007 | Worley |
| 2007/0208386 A1 | 9/2007 | Kramer et al. |
| 2008/0009909 A1 | 1/2008 | Sathaye et al. |
| 2008/0082133 A1 | 4/2008 | Zhou |
| 2008/0228234 A1 | 9/2008 | Stancer |
| 2008/0269816 A1 | 10/2008 | Prakash et al. |
| 2008/0269823 A1 | 10/2008 | Burnes et al. |
| 2008/0294210 A1 | 11/2008 | Rosero |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0281587 A1* | 11/2009 | Pei .................. A61B 5/04525 607/9 |
| 2010/0016914 A1 | 1/2010 | Mullen et al. |
| 2010/0023078 A1 | 1/2010 | Dong et al. |
| 2010/0185111 A1 | 7/2010 | Miller |
| 2010/0198291 A1 | 8/2010 | Sambelashvili et al. |
| 2010/0228308 A1 | 9/2010 | Cowan et al. |
| 2010/0286541 A1 | 11/2010 | Musley et al. |
| 2011/0071586 A1 | 3/2011 | Jacobson |
| 2011/0125078 A1 | 5/2011 | Denison et al. |
| 2011/0190841 A1 | 8/2011 | Sambelashvili et al. |
| 2011/0196444 A1 | 8/2011 | Prakash et al. |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0172892 A1 | 7/2012 | Grubac et al. |
| 2012/0263218 A1 | 10/2012 | Dal Molin et al. |
| 2012/0296228 A1 | 11/2012 | Zhang et al. |
| 2012/0316613 A1 | 12/2012 | Keefe et al. |
| 2013/0006622 A1 | 1/2013 | Khalil et al. |
| 2013/0013017 A1 | 1/2013 | Mullen et al. |
| 2013/0035748 A1 | 2/2013 | Bonner |
| 2013/0066169 A1 | 3/2013 | Rys et al. |
| 2013/0103109 A1 | 4/2013 | Jacobson |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0138006 A1 | 5/2013 | Bornzin et al. |
| 2013/0197599 A1 | 8/2013 | Sambelashvili et al. |
| 2013/0218223 A1 | 8/2013 | Ghosh et al. |
| 2013/0218224 A1 | 8/2013 | Ghosh et al. |
| 2013/0218225 A1 | 8/2013 | Ghosh et al. |
| 2013/0218226 A1 | 8/2013 | Ghosh et al. |
| 2013/0218227 A1 | 8/2013 | Ghosh et al. |
| 2013/0226259 A1 | 8/2013 | Penner |
| 2013/0231710 A1 | 9/2013 | Jacobson |
| 2013/0268017 A1 | 10/2013 | Zhang et al. |
| 2013/0282073 A1 | 10/2013 | Cowan et al. |
| 2014/0005740 A1 | 1/2014 | Ghosh et al. |
| 2014/0107723 A1 | 4/2014 | Hou et al. |
| 2014/0114372 A1 | 4/2014 | Ghosh et al. |
| 2014/0163635 A1 | 6/2014 | Ghosh et al. |
| 2014/0236253 A1 | 8/2014 | Ghosh et al. |
| 2014/0277233 A1 | 9/2014 | Ghosh |
| 2014/0277245 A1 | 9/2014 | Lu et al. |
| 2014/0277246 A1 | 9/2014 | Lu et al. |
| 2014/0330208 A1 | 11/2014 | Christie et al. |
| 2014/0330326 A1 | 11/2014 | Thompson-Nauman et al. |
| 2014/0358135 A1 | 12/2014 | Sambelashvili et al. |
| 2015/0142069 A1 | 5/2015 | Sambelashvili |
| 2015/0142070 A1 | 5/2015 | Sambelashvili |

FOREIGN PATENT DOCUMENTS

| | | |
|---|---|---|
| EP | 1 629 863 | 3/2006 |
| WO | 2001058518 A3 | 1/2002 |
| WO | 200247761 A2 | 6/2002 |
| WO | 2012128836 A1 | 9/2012 |

OTHER PUBLICATIONS

U.S. Appl. No. 14/261,460, filed Apr. 25, 2014, entitled "Implantable Medical Device System Having Implantable Cardiac Defibrillator System and Substernal Leadless Pacing Device".

U.S. Appl. No. 14/257,462, filed Apr. 21, 2014 entitled "Anchoring an Implantable Medical Device Within a Substernal Space".

Greenhut, et al., Method and Apparatus for Selection and Use of Virtual Sensing Vectors, U.S. Appl. No. 14/524,090, filed Oct. 27, 2014, 57pp.

PCT Publication which includes international search report, 42 pages, published Sep. 17, 2009.

Raul Chirife, M.D., et al., "Prediction of Interatrial and Interventricular Electromechanical delays from P/QRS Measurements: Value for Pacemaker Timing Optimization", Feb. 2008, Pacing and Clinical Electrophysiology: PACE, vol. 31, No. 2, pp. 177-183.

(PCT/US2014/066792) PCT Notification of Transmittal of the International Search Report and the Written Opinion of the International Searching Authority.

(PCT/US2013/013601) PCT Notification of Transmittal of the International Search Report and the Written Opinion of the International Searching Authority.

Rodney Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

(PCT/US2009/035698) International Search Report and the Written Opinion of the International Searching Authority, dated Oct. 14, 2009, 12 pages.

St. Jude's Quadra Assura MP with MultiPoint Pacing Gets European Go Ahead http://www.medgadget.com/2013/06/st-judes-quadra-assura-mp-with-multipoint-pacing-gets-european-go-ahead.html.

(PCT/US2016/042283) PCT Notification of Transmittal of the International Search Report and the Written Opinion of the International Searching Authority, dated Oct. 24, 2016, 10 pages.

\* cited by examiner

CONFIRMING SENSED ATRIAL EVENTS FOR PACING DURING RESYNCHRONIZATION THERAPY IN A CARDIAC MEDICAL DEVICE AND MEDICAL DEVICE SYSTEM

FIELD OF THE DISCLOSURE

The present disclosure pertains to cardiac pacing methods and systems, and, more particularly, to cardiac resynchronization therapy in a cardiac medical device system.

BACKGROUND OF THE DISCLOSURE

Implantable pacemakers and cardioverter defibrillators (ICDs) are available for delivering electrical stimulation therapies to a patient's heart, such as bradycardia pacing, cardiac resynchronization therapy (CRT), anti-tachycardia pacing and cardioversion/defibrillation shocks. Medical device technology advancement has led toward smaller and smaller implantable devices. Recently, leadless intracardiac pacemakers have been introduced which can be implanted directly in a heart chamber. Elimination of transvenous, intracardiac leads has several advantages. For example, complications due to infection associated with a lead extending from a subcutaneous pacemaker pocket transvenously into the heart can be eliminated. Other complications such as "twiddler's syndrome", lead fracture or poor connection of the lead to the pacemaker are eliminated in the use of a leadless, intracardiac pacemaker.

New challenges arise, however, in controlling an intracardiac pacemaker to deliver pacing pulses in synchrony with paced or sensed events occurring in other heart chambers. Cardiac resynchronization therapy (CRT) is an example of a pacing therapy that includes delivering pacing pulses in a heart chamber at a predetermined time interval after a sensed or paced event in another heart chamber. CRT is a treatment for heart failure patients in whom one or more heart chambers are electrically paced to restore or improve heart chamber synchrony. Improved heart chamber synchrony is expected to alleviate symptoms of heart failure. Achieving a positive clinical benefit from CRT, however, may be dependent on several therapy control parameters, such as the timing intervals used to control pacing pulse delivery, e.g., an atrio-ventricular (AV) interval and/or an inter-ventricular (VV) interval. The AV interval controls the timing of ventricular pacing pulses relative to a preceding atrial depolarization, intrinsic or paced. The VV interval controls the timing of a pacing pulse in one ventricle relative to a paced or intrinsic sensed event in the other ventricle. Pacing may be delivered in the right ventricle (RV) and/or the left ventricle (LV) to restore ventricular synchrony.

Cardiac resynchronization utilizing cardiac pacing therapy and cardiac pacing devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. In order to ensure the desired evoked response takes place, it is desirable to time the delivery of the ventricular pacing so as to be delivered at a point in time subsequent to a P-wave, resulting in the delivery of the pacing therapy coinciding with the occurrence of an R-wave of the cardiac cycle of the patient. As a result, the ability to sense P-waves is an important factor in determining timing of the ventricular pacing therapy for cardiac resynchronization therapy (CRT). Furthermore, when either a subcutaneous device or far-field signals are utilized, the R-waves and T-waves of the cardiac cycle are often either only slightly larger or of comparable magnitudes as P-waves, making distinguishing P-waves from R-waves and T-waves even more difficult. Therefore, what is needed is an improved method of distinguishing P-waves of a cardiac cycle for timing of delivery of ventricular pacing during CRT therapy.

DETAILED DESCRIPTION OF EXEMPLARY EMBODIMENTS

In the following detailed description, references are made to illustrative embodiments for carrying out methods of delivering atrial synchronous pacing with sensing of atrial activity from subcutaneous or far-field signals reflecting electrical activity of the different heart chambers. It is understood that other embodiments may be utilized without departing from the scope of the invention. For example, the invention is disclosed in detail herein in the context of a bi-ventricular or multi-electrode/multi-site cardiac resynchronization therapy (CRT) delivery.

Exemplary methods, devices, and systems shall be described with reference to FIGS. 1-7. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

Figure 1:
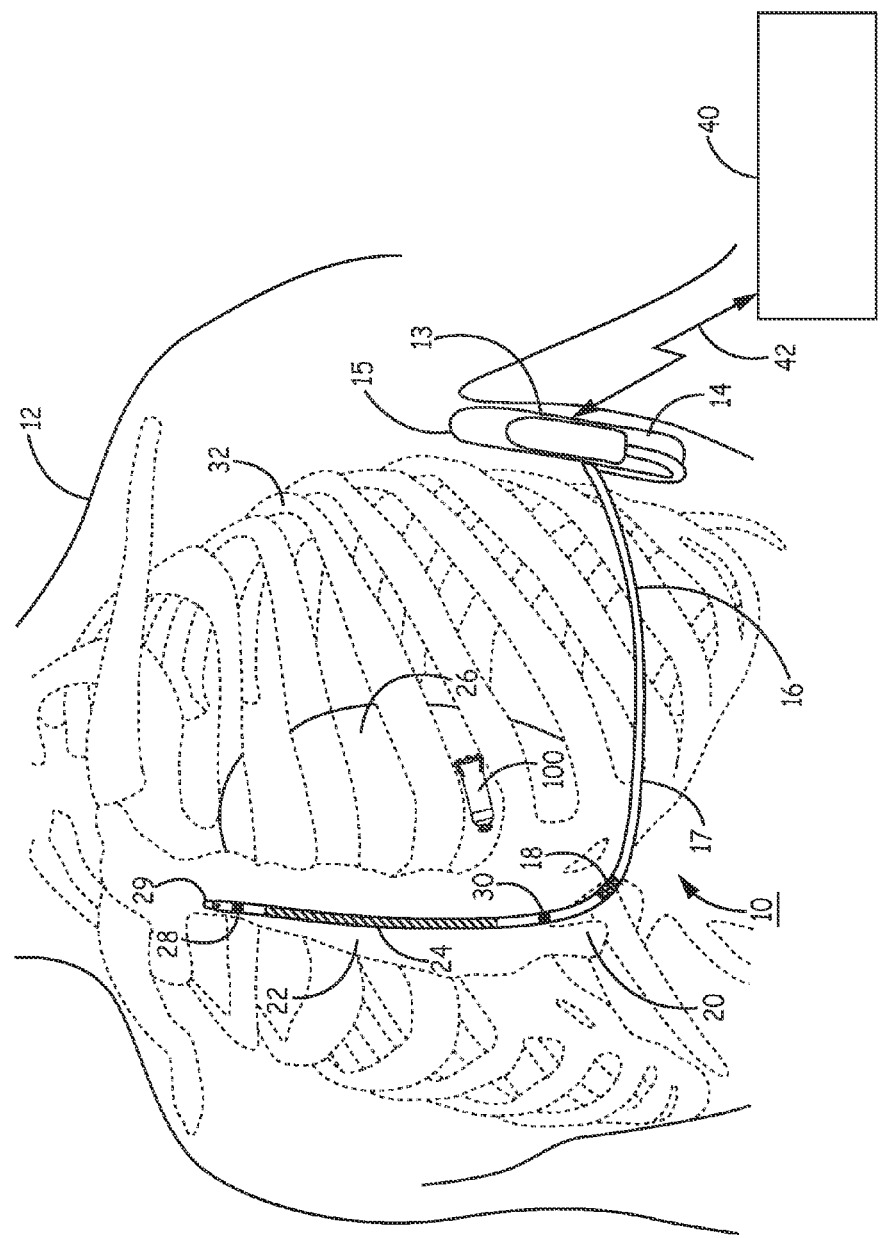
FIG. 1 is a conceptual diagram illustrating an implantable medical device (IMD) system that may be used to sense cardiac electrical signals in patient and provide therapy to the patient's heart.

FIG. 1 is a conceptual diagram illustrating an implantable medical device (IMD) system that may be used to sense cardiac electrical signals in patient and provide therapy to the patient's heart. As illustrated in FIG. 1, an implantable medical device (IMD) system 10 for confirming sensed atrial events for pacing and resynchronization therapy may include a therapy delivery device 100, such as an intracardiac pacemaker and a cardiac sensing device 14, such as a subcutaneous cardiac defibrillator coupled to an extravascular lead 16, such as a subcutaneous device implanted subcutaneously on the left side of a patient 12. Such a medical device system 10 is described, for example, in commonly assigned U.S. application patent Ser. No. 14/695,004, incorporated herein by reference in it's entirety. While the subcutaneous device is shown implanted subcutaneously on the left side of a patient 12, it is understood that sensing device 14 and lead 16 may be implanted at other locations, such as the right side of patient 12, for example. The cardiac sensing device 14 includes a defibrillation lead 16 having a defibrillation electrode 24 positioned along a proximal end of the lead 16, which may be an elongated coil electrode, a pair of sensing electrodes 28 and 30, illustrated as ring electrodes, although other electrode configurations may be utilized, and a trigger signal emitting device 18. Trigger signal emitting device 18 includes a transducer that is controlled by cardiac sensing device 14 to emit trigger signals received by therapy delivery device 100 to cause therapy delivery device 100 to deliver one or more pacing pulses.

Defibrillation lead 16, which is connected to cardiac sensing device 14, extends medially from cardiac sensing device 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 is over sternum 22 or offset laterally to the left or right side of the body of sternum 22, and may be implanted subcutaneously, e.g., between the skin and the ribs or sternum. Defibrillation lead 16 may be implanted at other locations or angles relative to sternum 22, or positioned further superior or inferior, depending on the location of cardiac sensing device 14, position of electrodes 24, 28, and 30 and trigger signal emitting device 18 along lead 16, the location of pacemaker 100, or other factors. In other instances, lead 16 may be implanted at other extravascular locations. In one example, lead 16 may be implanted at least partially in a substernal location or within ribcage 32, within the thoracic cavity, and within or outside the pericardium, not necessarily in direct contact with heart 26.

Defibrillation lead 16 is placed along sternum 22 such that a therapy vector between defibrillation electrode 24 and a second electrode (such as a portion of the housing 15 of cardiac sensing device 14 or an electrode placed on a second lead) is substantially across one or both ventricles of heart 26. The therapy vector may, in one example, be viewed as a line that extends from a point on the defibrillation electrode 24 to a point on the housing 15 (sometimes referred to as "can electrode") of cardiac sensing device 14. In another example, defibrillation lead 16 may be placed along sternum 22 such that a therapy vector between defibrillation electrode 24 and housing 15 of cardiac sensing device 14 (or other electrode) is substantially across an atrium of heart 26. In this case, system 10 may be used to provide atrial therapies, such as therapies to treat atrial fibrillation.

Trigger signal emitting device 18 is positioned to establish a trigger signal transmission pathway that does not excessively attenuate the trigger signal transmitted from emitting device 18 to a receiver or detector included in intracardiac therapy delivery device 100. For example, the location of emitting device 18 may be selected so that a direct pathway between emitting device 18 and therapy delivery device 100 avoids, as much as possible, tissues that are highly reflective, scattering or absorbing of the type of trigger signal being used. When lead 16 is positioned extra-thoracically, emitting device 18 may be positioned inferior to the xyphoid process 20 in a position approximately as shown. Emitting device 18 is positioned relative to therapy delivery device 100 to establish an efficient trigger signal transmission pathway, which may be a direct or indirect pathway that takes into account the trigger signal properties and the transmission or attenuation properties of the surrounding and intervening tissues for the type of trigger signal being used.

Defibrillation lead 16 may include an attachment feature 29 at or toward the distal end of lead 16. The attachment feature 29 may be a loop, link, or other attachment feature useful to aid in implantation of lead 16 and/or for securing lead 16 to a desired implant location. In some instances, defibrillation lead 16 may include a fixation mechanism in addition to or instead of the attachment feature 29. For example, defibrillation lead 16 may include a suture sleeve or other fixation mechanism (not shown) located proximal to electrode 30 or near emitting device 18 that is configured to fixate lead 16 near the xiphoid process 20 or lower sternum location. The fixation mechanism (e.g., suture sleeve or other mechanism) may be integral to the lead or may be added by the user prior to implantation. The fixation mechanism may be used to stably locate emitting device 18 inferior to the xyphoid process 20, along an intercostal space, or other desired location to prevent rotation or shifting of the emitting device 18 that may cause trigger signal misdirection or trigger signal loss due to interference or attenuation by body tissues.

Although cardiac sensing device 14 is illustrated as being implanted near a midaxillary line of patient 12, cardiac sensing device 14 may also be implanted at other subcutaneous locations on patient 12, such as further posterior on the torso toward the posterior axillary line, further anterior on the torso toward the anterior axillary line, in a pectoral region, or at other locations of patient 12. In instances in which cardiac sensing device 14 is implanted pectorally, lead 16 would follow a different path, e.g., across the upper chest area and inferior along sternum 22. When the cardiac sensing device 14 is implanted in the pectoral region, the system 10 may include a second lead including a defibrillation electrode, and optionally a trigger signal emitting device, that extends along the left side of the patient such that the defibrillation electrode of the second lead is located along the left side of the patient to function as an anode or cathode of the therapy vector for defibrillating heart 26.

Cardiac sensing device 14 includes a housing 15 that forms a hermetic seal that protects components within cardiac sensing device 14. The housing 15 of cardiac sensing device 14 may be formed of a conductive material, such as titanium or other biocompatible conductive material or a combination of conductive and non-conductive materials. Housing 15 may enclose one or more components, including processors, memories, transmitters, receivers, sensors, sensing circuitry, therapy circuitry and other appropriate components (often referred to herein as modules). In some instances, the housing 15 functions as an electrode (sometimes referred to as a housing electrode or can electrode) that is used in combination with one of electrodes 24, 28 and 30 to deliver a therapy to heart 26 or to sense electrical activity of heart 26.

Cardiac sensing device 14 may include a connector assembly 13 (sometimes referred to as a connector block or header) for receiving a proximal connector (not illustrated) of lead 16. Connector assembly 13 includes electrical feedthroughs through which electrical connections are made between conductors within defibrillation lead 16 and electronic components included within the housing 15. Depending on the intended implant location of cardiac sensing device 14, a trigger signal emitting device may be included in connector assembly 13 and/or housing 15 in addition to or in place of the emitting device 18 carried by lead 16 for transmitting trigger signals to therapy delivery device 100.

Lead 16 includes a connector at the proximal end of lead 16, such as a DF4 connector, bifurcated connector (e.g., DF-1/IS-1 connector), or other type of connector. The connector at the proximal end of lead 16 may include a terminal pin that couples to a port within the connector assembly 13 of cardiac sensing device 14. The lead body 17 of defibrillation lead 16 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

Defibrillation lead 16 includes elongated electrical conductors (not illustrated) that extend within the elongated lead body 17 from the connector on the proximal end of defibrillation lead 16 to the respective electrodes 24, 28 and 30 and emitting device 18. Although defibrillation lead 16 is illustrated as including three electrodes 24, 28 and 30, defibrillation lead 16 may include more or fewer electrodes. When the connector at the proximal end of defibrillation lead 16 is connected to connector assembly 13, the respective conductors electrically couple to circuitry of cardiac sensing device 14, such as a therapy delivery module, a sensing module, or trigger signal drive signal circuit, via connections in connector assembly 13, including associated feedthroughs.

The electrical conductors transmit electrical stimulation pulses from a therapy module within cardiac sensing device 14 to one or more of electrodes 24, 28 and 30 and transmit sensed electrical signals from one or more of electrodes 24, 28 and 30 to the sensing module within cardiac sensing device 14. An electrical conductor extending from the proximal lead connector to emitting device 18 conducts an electrical control signal to emitting device 18 to cause emitting device 18 to emit a trigger signal at appropriate times for causing intracardiac therapy delivery device 100 to deliver one or more pacing pulses to heart 26.

Cardiac sensing device 14 may sense electrical activity of heart 26 via one or more sensing vectors that include combinations of electrodes 28 and 30 and housing 15. For example, cardiac sensing device 14 may obtain cardiac electrical signals sensed using a sensing vector between electrodes 28 and 30, between electrode 28 and the conductive housing 15, between electrode 30 and the conductive housing 15, or any combination thereof. In some instances, cardiac sensing device 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15 of cardiac sensing device 14.

Cardiac sensing device 14 determines a need for pacing therapy in response to the sensed cardiac electrical signals, which may include P-waves and R-waves for example, and controls emitting device 18 to emit trigger signals based on that determination. The need for pacing pulses may be determined according to programmed single chamber, dual chamber or multi-chamber bradycardia or CRT control parameters or other cardiac pacing therapy parameters. Cardiac sensing device 14 may also analyze the sensed electrical signals to detect tachyarrhythmia, such as ventricular tachycardia or ventricular fibrillation, and in response to detecting tachyarrhythmia may generate and deliver an electrical stimulation therapy to heart 26. For example, cardiac sensing device 14 may deliver one or more defibrillation shocks via a therapy vector that includes defibrillation electrode 24 of defibrillation lead 16 and the housing 15.

Electrodes 24, 28, 30 and housing 50 may be used for sensing ECG signals for use in controlling the timing of an R-wave synchronized shock delivered by cardiac sensing device 14 and for controlling timing of pacing pulses delivered by therapy delivery device 100. In some instances, one or more pacing therapies may be delivered prior to or after delivery of a defibrillation shock by cardiac sensing device 14, such as anti-tachycardia pacing (ATP) or post shock pacing. In these instances, cardiac sensing device 14 may generate and deliver pacing pulses via therapy vectors that include electrodes 24, 28, 30 and/or housing 15. Alternatively, cardiac sensing device 14 causes trigger signal emitting device 18 to emit trigger signals to cause therapy delivery device 100 to deliver pacing pulses to heart 26 at appropriate times when ATP or post-shock pacing is needed as well as when bradycardia or CRT pacing therapy is needed.

The exemplary cardiac sensing device 14 illustrated in FIG. 1 is illustrative in nature and should not be considered limiting of the sensing device used in a triggered therapy delivery system and associated techniques described in this disclosure. For instance, in addition to sensing ECG signals, cardiac sensing device 14 may include shock therapy capabilities only without pacing therapy capabilities. In other examples, cardiac sensing device 14 may be coupled to more than one lead for sensing ECG signals and/or sending trigger signals to therapy delivery device 100. In still other examples, a sensing device may be substituted for cardiac sensing device 14 that is a single chamber or dual chamber subcutaneous pacemaker without cardioversion/defibrillation capabilities or a sensing-only device without therapy delivery capabilities. Any of these sensing devices may be coupled to housing-based electrodes and/or electrodes carried by a transvenous, intracardiac or extravascular, extracardiac lead for sensing a cardiac electrical signal and determining appropriate times for triggering therapy delivery device 100 to delivery therapy. In another embodiment, the sensing device may be a subcutaneously implanted leadless device, such as the leadless subcutaneous sensor device in commonly assigned U.S. patent application Ser. No. 14/695,004 to Carnet et. al, Ser. No. 14/695,013 to Cinbis et. al, for example, both incorporated by reference in their entireties.

Therapy delivery device 100 may be a transcatheter intracardiac pacemaker adapted for implantation wholly within a heart chamber, e.g., wholly within the RV, wholly within the LV, wholly within the right atrium (RA) or wholly within the left atrium (LA) of heart 26. In the example of FIG. 1, therapy delivery device 100 is positioned proximate to an inner wall of the LV to provide left ventricular pacing. In other examples, therapy delivery device 100 is positioned proximate to an inner wall of the right ventricle to provide right ventricular pacing. In other examples, therapy delivery device 100 may be positioned at any other location outside or within heart 26, including epicardial locations. For example, therapy delivery device 100 may be positioned outside or within the right atrium or left atrium, e.g., to provide respective right atrial or left atrial pacing. In other embodiments, therapy delivery device 100 may be embodied as a therapy delivery device for delivering an electrical stimulation therapy at another body location. Therapy delivery device 100 is shown as a leadless device in FIG. 1. It is contemplated, however that in other embodiments therapy delivery device 100 may be coupled to a lead extending from therapy deliver device 100 to position therapy delivery electrodes at a location spaced apart from therapy delivery device 100.

Depending on the implant location, therapy delivery device 100 may be configured to deliver an electrical stimulation therapy to target therapy site(s) other than the myocardium. For example, therapy delivery device 100 may provide atrioventricular nodal stimulation, fat pad stimulation, vagal stimulation, or other types of neurostimulation. In other examples, system 10 may include a plurality of pacemakers 100, e.g., to deliver electrical stimulation therapy at multiple sites of heart 26 such as within multiple heart chambers for multi-chamber pacing therapies.

Therapy delivery device 100 is capable of producing electrical stimulation pulses delivered to heart 26 via one or more electrodes on the outer housing of therapy delivery device 100. Therapy delivery device 100 includes a receiving transducer for receiving a trigger signal emitted by emitting device 18. In response to detecting the trigger signal, therapy delivery device 100 delivers one or more pacing pulses.

In one embodiment, therapy delivery device 100 includes a pulse generator configured to deliver one or more pacing pulses upon receiving the trigger signal from emitting device 18. Cardiac signal sensing is performed by cardiac sensing device 14. Cardiac sensing device 14 senses ECG signals through lead 16 and controls pacing delivered by therapy delivery device 100 via trigger signals emitted by emitting device 18 under the control of cardiac sensing device 14.

Since therapy delivery device 100 may have no or limited sensing capabilities, therapy delivery device 100 may be "blinded" to intrinsic events, such as intrinsic R-waves, occurring in the same heart chamber and to paced or intrinsic events occurring in other heart chambers. Delivery of CRT, dual chamber pacing, or other multi-chamber pacing therapies may require delivering a pacing pulse at a predetermined time interval after an event, sensed or paced, in another heart chamber. As such, emitting device 18 provides a trigger signal to therapy delivery device 100 in response to ECG signals sensed by cardiac sensing device 14 to cause pacing pulses to be delivered by therapy delivery device 100 at desired time intervals relative to other heart chamber events. Therapy delivery device 100 (for generating pacing pulses) combined with cardiac sensing device 14 (for sensing physiological signals and making therapy delivery decisions) provides the functionality required to deliver various therapies that may require synchronization or coordination with cardiac events occurring in the same or a different heart chamber without physical connection between therapy delivery device 100 and cardiac sensing device 14 implanted at separate implant sites.

FIG. 1 further depicts programmer 40 in wireless communication with cardiac sensing device 14 via communication link 42. In some examples, programmer 40 comprises a handheld computing device, computer workstation, or networked computing device. Programmer 40 includes a user interface that presents information to and receives input from a user. It should be noted that the user may also interact with programmer 40 remotely via a networked computing device.

A user, such as a physician, technician, surgeon, electrophysiologist, other caregiver, or patient, interacts with programmer 40 to communicate with cardiac sensing device 14. For example, the user may interact with programmer 40 to retrieve physiological or diagnostic information from cardiac sensing device 14. A user may also interact with programmer 40 to program cardiac sensing device 14, e.g., select values for operational parameters of the cardiac sensing device 14, including parameters used to control trigger signal emitting device 18 for controlling therapy delivery device 100. A user may use programmer 40 to retrieve information from cardiac sensing device 14 regarding the rhythm of heart 26, heart rhythm trends over time, or arrhythmic episodes.

As indicated, cardiac sensing device 14 and programmer 40 communicate via wireless communication. Examples of communication techniques may include low frequency or radiofrequency (RF) telemetry, but other techniques may be used. In some examples, programmer 40 may include a programming head that is placed proximate to the patient's body near the cardiac sensing device 14 implant site in order to improve the quality or security of communication between cardiac sensing device 14 and programmer 40.

The embodiment illustrated in FIG. 1 is an example configuration of an IMD system 10 and should not be considered limiting of the techniques described herein. In other embodiments, cardiac sensing device 14 may be coupled to a transvenous intracardiac lead extending into the right ventricle (RV) for positioning RV sensing and pacing electrodes and a defibrillation coil electrode within the RV. An example of an RV lead that could be adapted to carry an emitting device 18 is generally disclosed in commonly-assigned, U.S. Pat. No. 5,545,186 (Olson, et al.). In this example, emitting device 18 may be positioned more distally than the position shown on lead 16 such that the emitting device 18 is positioned in the RV, opposite therapy delivery device 100 in the LV. Emitting device 18 may then be enabled to emit a trigger signal from the RV to the therapy delivery device 100 in the LV to coordinate timing of the LV pacing pulse relative to a right atrial event or a right ventricular event. It is contemplated that numerous configurations of a lead-based emitting device 18 may be conceived and emitting device 18 may be positioned along the lead body 17 at relatively more proximal or more distal locations than shown on lead 16 to position emitting device 18 at a desired location relative to therapy delivery device 100.

Figure 2:
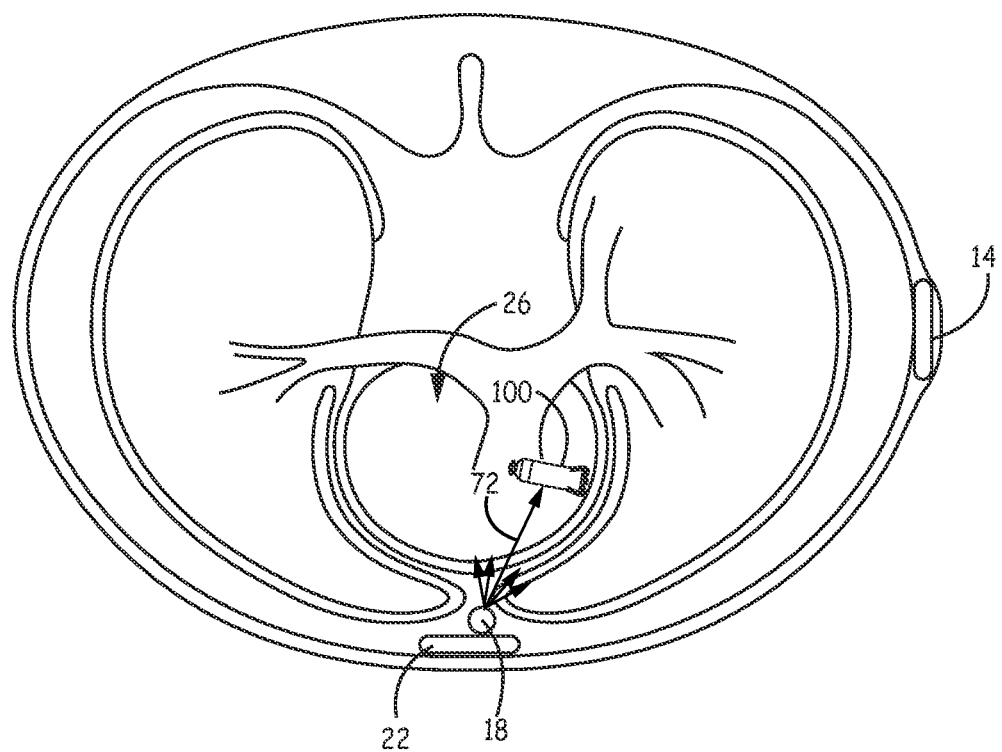
FIG. 2 is a sectional view of the patient's anatomy depicting an alternative configuration of the implantable medical device system of FIG. 1.

FIG. 2 is a sectional view of the patient's anatomy depicting an alternative configuration of the implantable medical device system of FIG. 1. Emitting device 18 is shown in a substernal position on lead 16 (not seen in the sectional view of FIG. 2). Instead of being positioned suprasternally, inferior to the xyphoid process, emitting device 18 may be positioned substernally and relatively more superior by advancing the distal end of lead 16 to a substernal location. Emitting device 18 may be configured for directional trigger signal emission with emitting device 18 oriented to generally direct the trigger signal toward the implant position of therapy delivery device 100, e.g., along a signal pathway to therapy delivery device 100 as represented by arrow 72.

Lead 16 may be placed under or below the sternum in the mediastinum and, more particularly, in the anterior mediastinum. The anterior mediastinum is bounded laterally by pleurae, posteriorly by pericardium, and anteriorly by sternum. Lead 16 may be at least partially implanted in other extra-pericardial locations, i.e., locations in the region around, but not necessarily in direct contact with, the outer surface of heart 26. These other extra-pericardial locations may include in the mediastinum but offset from sternum 22, in the superior mediastinum, in the middle mediastinum, in the posterior mediastinum, in the sub-xiphoid or inferior xiphoid area, near the apex of the heart, or other location not in direct contact with heart 26 and not subcutaneous. In other embodiments, lead 16 may extend within the pericardium and in direct contact with heart 26. In any of these illustrative implant locations, lead 16 may be positioned to optimally position trigger signal emitting device 18 for reliably transmitting a trigger signal to therapy delivery device 100.

Figure 3:
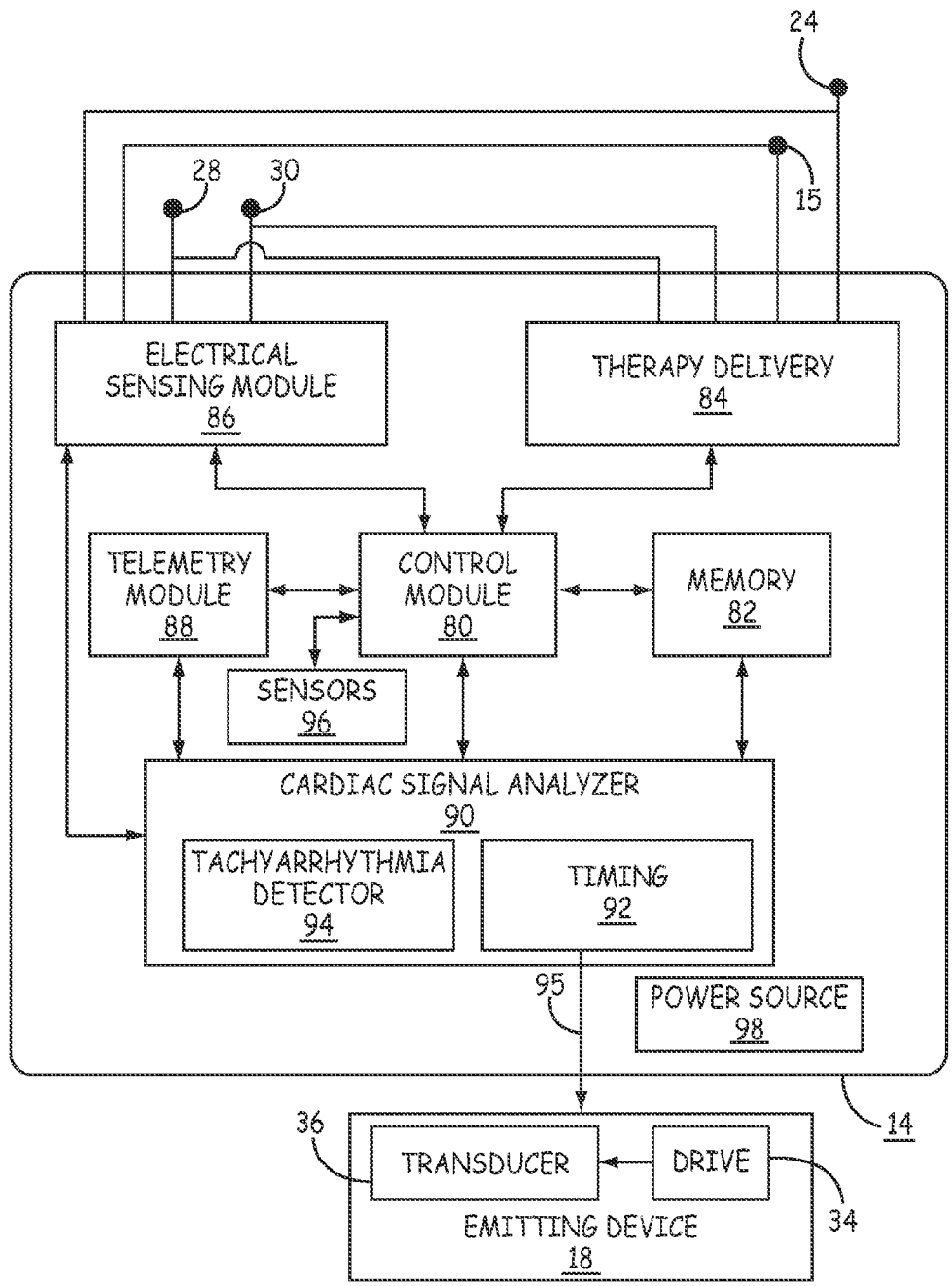
FIG. 3 is a functional block diagram of electronic circuitry that is included in one embodiment of the implantable medical device system shown in FIGS. 1 and 2.

FIG. 3 is a functional block diagram of electronic circuitry that is included in one embodiment of the implantable medical device system shown in FIGS. 1 and 2. As illustrated in FIG. 3, ICD 14 includes processing and control module 80, also referred to as "control module" 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, 90. Power source 98 may include one or more energy storage devices, such as one or more chargeable or non-re-chargeable batteries.

The functional blocks shown in FIG. 3 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, memory devices, etc. Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal. The particular form of software, hardware and/or firmware employed to implement the functionality disclosed herein will be determined primarily by the particular system architecture employed in the IMD system devices. Providing software, hardware, and/or firmware to accomplish the described functionality in the context of any modern IMD system, given the disclosure herein, is within the abilities of one of skill in the art.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, arrhythmia detection operations performed by cardiac signal analyzer 90 for determining a need for therapy delivered by ICD 14 and/or therapy delivery device 100 may be implemented in processing and control module 80 executing instructions stored in memory 82.

Processing and control module 80 communicates with therapy delivery module 84, cardiac signal analyzer 90 and electrical sensing module 86 for sensing cardiac electrical activity, detecting cardiac rhythms, and generating cardiac therapies in response to sensed signals. Therapy delivery module 84 and electrical sensing module 86 are electrically coupled to electrodes 24, 28, and 30 carried by lead 16, e.g., as shown in FIG. 1, and housing 15, at least a portion of which also serves as a common or ground electrode.

Electrical sensing module 86 is coupled to electrodes 28 and 30 in order to monitor electrical activity of the patient's heart. Electrical sensing module 86 may optionally be coupled to electrodes 24 and 15 and enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers included in sensing module 86. Switching circuitry may include a switch array, switch matrix, multiplexer, or any other type of switching device suitable to selectively couple sense amplifiers to selected electrodes. A sensing vector between electrodes 28 and 30 may be selected for sensing an ECG signal, although it is recognized that in some embodiments sensing vectors may be selected that utilize coil electrode 24 and/or housing electrode 15, e.g., from electrode 28 to housing 15 or electrode 30 and housing 15.

One or more ECG signals are received by an input of sensing module 86. Sensing module 86 includes one or more sense amplifiers or other cardiac event detection circuitry for sensing cardiac events, e.g., P-waves or R-waves, from the ECG signal(s). Sensing module 86 passes sense event signals to cardiac signal analyzer 90 in response to sensing cardiac events. For example P-wave sense event signals and R-wave sense event signals are passed to cardiac signal analyzer 90 when the ECG signal crosses a respective P-wave sensing threshold and R-wave sensing threshold, which may each be auto-adjusting sensing thresholds. Bradycardia or asystole is typically determined by a pacing escape interval timer expiring within the timing circuit 92. In response to the pacing escape interval expiring, a control signal 95 is passed to the trigger signal emitting device 18. The pacing escape interval is restarted upon a trigger signal or a sense event signal.

The control signal 95 in the illustrative examples presented herein may be referred to as a pacing control signal because it causes therapy delivery device 100 to deliver a pacing pulse to a heart chamber. In other examples, the control signal 95 may be produced by cardiac signal analyzer 90 to cause other types of therapy pulses to be delivered by therapy delivery device 100 (or another therapy delivery device). For example control signal 95 may be produced to cause therapy delivery device 100 or another therapy delivery device to deliver an ATP pulse, a vagal nerve stimulation pulse, or other type of electrical stimulation pulse.

The control signal 95 is an electrical signal that is passed to emitting device 18 along lead 16 or 60 (or another lead carrying emitting device 18) when emitting device 18 is coupled to ICD 14 in a wired connection. The control signal 95 is alternatively a wireless telemetry signal that is transmitted via telemetry module 88, to emitting device 18. Emitting device 18 may be carried by a lead but configured to wirelessly receive a control signal 95 from telemetry module 88. Alternatively, the emitting device 18 is not a lead-based emitting device and receives control signal 95 wirelessly, e.g., as an RF telemetry signal, from telemetry module 88. It is understood that in some embodiments, drive signal circuit 34 may be included within the housing 15 of ICD 14 and coupled to transducer 36 located external to housing 15.

Trigger signal emitting device 18 includes a drive signal circuit 34 that receives the control signal 95, either as a wired electrical signal or a wireless signal from telemetry module 88. Drive signal circuit 34 passes an electrical signal to transducer 36 to enable transducer 36 to emit the trigger signal. Transducer 36 may be an optical transducer or an acoustical transducer in various examples. In other examples, the drive signal circuit 34 is coupled to an antenna for transmitting the trigger signal as an RF signal.

The trigger signal is received and detected by therapy delivery device 100 causing therapy delivery device 100 to deliver one or more pacing pulses to the patient's heart. In some examples, the trigger signal is generated according to predetermined frequency, amplitude, duration and other characteristics that are not intentionally varied by emitting device 18 under the control signal 95. In other words, the trigger signal merely signals therapy delivery device 100 to deliver therapy without any information relating to how many pacing pulses, what pulse amplitude or pulse width or other pacing pulse control parameters. Therapy delivery device 100 is programmed to deliver a predetermined number of pacing pulses according to predefined pulse control parameters when the trigger signal is detected.

Alternatively, control signal 95 may include encoded pacing pulse control information. The control signal 95 generated by drive circuit 34 may cause transducer 36 to emit a trigger signal according to a frequency, duration, amplitude or other intentionally varied characteristics of the trigger signal to include pacing pulse control parameter information. As described below, a parameter of the trigger signal emitted by transducer 36 may be controllably varied by control signal 95 and drive circuit 34 to cause therapy delivery device 100 to adjust a pacing pulse control parameter such as pacing pulse width, pulse number, etc. Trigger signal parameters that may be varied under the control of signal 95 and drive circuit 34 include, without limitation, trigger signal amplitude, signal frequency, pulse width, pulse number and interpulse interval.

Transducer 36 may be embodied as one or more transducers configured to emit sound or light, for example, upon receiving a drive signal from circuit 34. Transducer 36 may include any combination of one or more of a ceramic piezoelectric crystal, a polymer piezoelectric crystal, capacitive micromachined ultrasonic transducer (CMUT), piezoelectric micromachined ultrasonic transducer (PMUT), or other ultrasonic transducer, a light emitting diode (LED), a vertical cavity surface emitting laser (VCSEL) or other light source having a high quantum efficiency at a selected light wavelength. Transducer 36 may include multiple transducers arranged in an array and/or configured to emit signals in multiple directions from emitting device 18 to promote reception of the trigger signal by therapy delivery device 100 despite shifting, rotation or other changes of the relative orientations of emitting device 18 and therapy delivery device 100 with respect to each other. The multiple transducers may be selectable by drive circuit 34 such that a single one or combination of transducers producing the best signal-to-noise ratio at the pacemaker receiving transducer is selected.

In one example, transducer 36 may include multiple acoustic transducers activated by drive signal circuit 34 to emit sound waves that constructively interfere to improve the efficiency of acoustical signal transmission. Emitting device 18 is shown as a single device but may be implemented as more than one emitting device such that transmission of the trigger signal is distributed over two or more emitting devices. When two or more emitting devices are used, emitting device 18 may include one or more lead-based emitting devices, one or more leadless emitting devices, and/or one or more emitting devices incorporated in ICD 14. Two or more emitting devices may be activated synchronously to produce ultrasound waves that superimpose at the receiver of therapy delivery device 100 to increase transmission efficiency and/or improve signal reception. A phased array of transducers that can be independently pulsed to emit sound can be used to focus the acoustical signal toward the intended receiving transducer in therapy delivery device 100. When multiple therapy delivery devices 100 or other therapy delivery devices are included, a phased array of transducers included in transducer 36 may be controlled by drive signal circuit 34 to pulse the transducers in a programmed time relationship to focus the trigger signal on the receiver of an intended therapy delivery device.

Transducer 36 may include multiple transducers having different properties for emitting different frequencies of sound, light or RF signal. The different transducers are selectable by drive circuit 34 to enable transmission of different frequencies of trigger signals. For example, different frequencies or different patterns of amplitude, frequency, pulse number, etc. may be emitted for triggering different responses by therapy delivery device 100 or for triggering different intracardiac pacemakers when multiple pacemakers are implanted. As indicated above, different trigger signals may be used to cause therapy delivery device 100 to deliver pacing pulses according to different pacing pulse control parameters, such as different pulse shape, pulse amplitude, pulse width, pulse rate or pulse number.

The transducer 36 is configured to emit a trigger signal at an amplitude and frequency that is detectable by a receiving transducer of therapy delivery device 100, after attenuation by body tissues along the pathway between the transducer 36 and the therapy delivery device 100. In one example, transducer 36 is configured to emit sounds in the range of approximately 40 kHz to over 1 MHz. An optical trigger signal may be emitted with a wavelength greater than approximately 1000 nm. An RF signal can be radiated from an antenna at frequencies between 400 MHz and 3 GHz. The frequency of the trigger signal is selected in part based on the types and thicknesses of body tissues encountered along the signal pathway.

Timing circuit 92 may generate control signal 95 to trigger therapy delivery device 100 to provide bradycardia pacing, anti-tachycardia pacing, cardiac resynchronization therapy, AV nodal stimulation, or other pacing therapies according to pacing algorithms and timing intervals stored in memory 82. Bradycardia pacing may be delivered by therapy delivery device 100 temporarily to maintain cardiac output after delivery of a cardioversion-defibrillation shock by ICD 14 as the heart recovers back to normal function post-shock.

Cardiac signal analyzer 90 includes a tachyarrhythmia detector 94 for detecting and discriminating supraventricular tachycardia (SVT), ventricular tachycardia (VT) and ventricular fibrillation (VF). Some aspects of sensing and processing subcutaneous ECG signals are generally disclosed in commonly-assigned U.S. Pat. No. 7,904,153 (Greenhut, et al.), hereby incorporated herein by reference in its entirety. The timing of R-wave sense event signals from sensing module 86 is used by tachyarrhythmia detector 94 to measure R-R intervals for counting RR intervals in different detection zones or determining a heart rate or other rate-based measurements for detecting ventricular tachyarrhythmia. Electrical sensing module 86 may additionally or alternatively provide digitized ECG signals to cardiac signal analyzer 90 for use in detecting tachyarrhythmia. Examples of ICDs that may be adapted for use with a triggered therapy delivery device 100 and operations that may be performed by tachyarrhythmia detector 94 for detecting, discriminating and treating tachyarrhythmia are generally disclosed in U.S. Pat. No. 7,742,812 (Ghanem, et al.), U.S. Pat. No. 8,160,684 (Ghanem, et al.), U.S. Pat. No. 5,354,316 (Keimel); U.S. Pat. No. 6,393,316 (Gillberg et al.), U.S. Pat. No. 5,545,186 (Olson, et al.), and U.S. Pat. No. 5,855,593 (Olson, et al.), all of which patents are incorporated herein by reference in their entirety.

The detection algorithms are highly sensitive and specific for the presence or absence of life threatening VT and VF. Therapy delivery module 84 includes a HV therapy delivery module including one or more HV output capacitors. When a malignant tachycardia is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy cardioversion/defibrillation shocks using coil electrode 24 and housing electrode 15.

It should be noted that implemented arrhythmia detection algorithms may utilize not only ECG signal analysis methods but may also utilize supplemental sensors 96, such as tissue color, tissue oxygenation, respiration, patient activity, heart sounds, and the like, for contributing to a decision by processing and control module 80 to apply or withhold a therapy. Sensors 96 may also be used in determining the need and timing for pacing by therapy delivery device 100. For example, an activity sensor signal or other rate responsive sensor signal, such as a minute ventilation signal, may be used for determining a pacing rate meeting a patient's metabolic demand. Timing circuit 92 produces a control signal 95 to cause emitting device 18 to generate trigger signals that cause therapy delivery device 100 to deliver pacing pulses at an appropriate rate based on the rate responsive signal. Sensors 96 may include one or more sensors carried by a lead extending from ICD 14 or within or along housing 15 and/or connector block 13.

Telemetry module 88 includes a transceiver and antenna for communicating with another device, such as an external programmer 40 and emitting device 18 when it is configured to receive control signal 95 wirelessly. Under the control of control module 80, telemetry module 88 may receive downlink telemetry from and send uplink telemetry to programmer 40 or another external device. Telemetry module 88 may transmit a control signal wirelessly to emitting device 18, e.g., as an RF signal.

Figure 4:
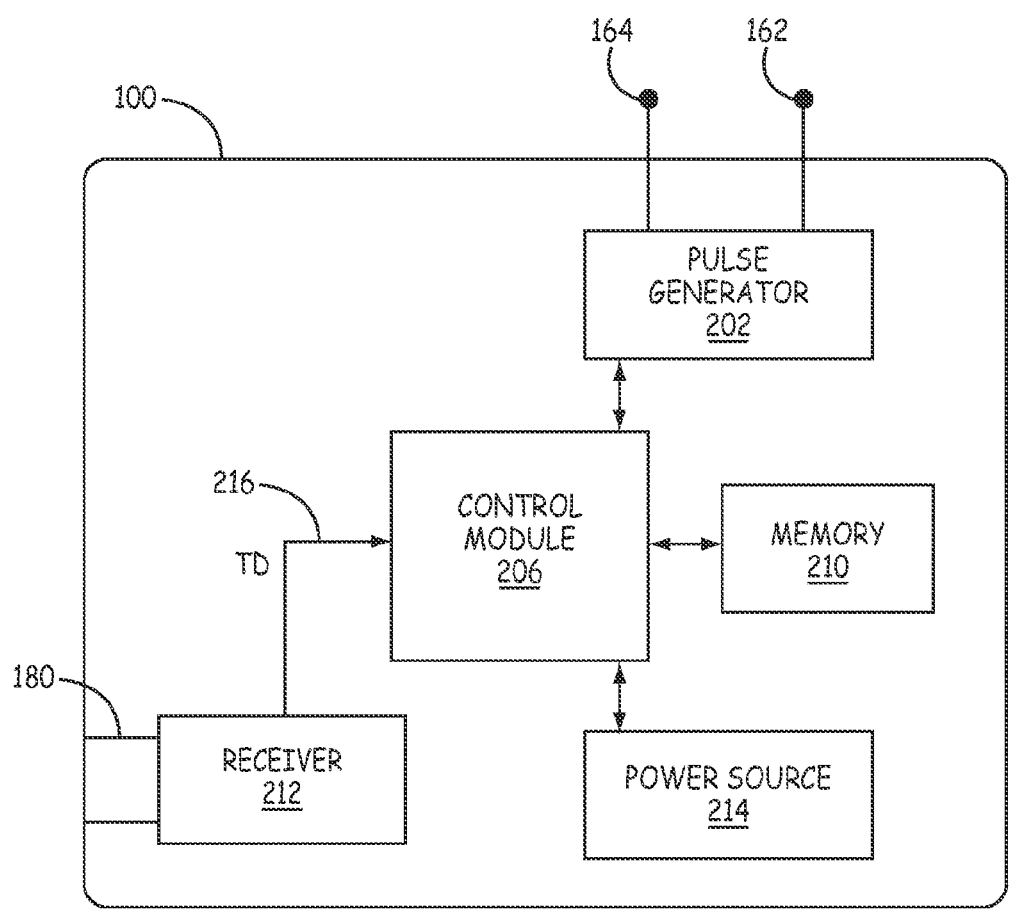
FIG. 4 is a functional block diagram of an example configuration of a therapy delivery device according to an embodiment of the present disclosure.

FIG. 4 is a functional block diagram of an example configuration of a therapy delivery device according to an embodiment of the present disclosure. As illustrated in FIG. 4, therapy delivery device 100 includes a pulse generator 202, an optional sensing module (not shown), a control module 206, memory 210, trigger signal receiver 212 and a power source 214. Pulse generator 202 generates electrical stimulation pulses that are delivered to heart tissue via electrodes 162 and 164. Control module 206 controls pulse generator 202 to deliver a stimulation pulse in response to receiving a trigger detect (TD) signal 216 from receiver 212. In other embodiments, pulse generator 202 may be configured to be enabled to deliver a stimulation pulse directly by an input signal received from receiver 212. For example, a switch responsive to a trigger detect signal 216 produced by receiver 212 may enable pulse generator 202 to deliver a stimulation pulse to a targeted tissue via electrodes 162 and 164.

Pulse generator 202 includes one or more capacitors and a charging circuit to charge the capacitor(s) to a pacing pulse voltage. The pacing capacitor may be charged to the pacing pulse voltage while control module 206 waits for a trigger detect signal 216 from receiver 212. Upon detecting the trigger signal, the capacitor is coupled to pacing electrodes 162, 164 to discharge the capacitor voltage and thereby deliver the pacing pulse. Alternatively, detection of the trigger signal initiates pacing capacitor charging and when a predetermined pacing pulse voltage is reached, the pulse is delivered. Pacing circuitry generally disclosed in U.S. Pat. No. 8,532,785 (Crutchfield), hereby incorporated herein by reference in its entirety, may be implemented in therapy delivery device 100 for charging a pacing capacitor to a predetermined pacing pulse amplitude under the control of control module 206 and delivering a pacing pulse.

Alternatively, pulse generator 202 may include a switch that connects power source 214 to pacing electrodes 162 and 164 to deliver the pacing pulse. The switch is opened by trigger detect signal 216 or by a control signal from control module 206, and power source 214 delivers energy to pulse generator 202 for generating a pacing pulse.

As described below, control module 206 may determine a pacing pulse control parameter from the trigger detect signal 216 and use the determined pacing pulse control parameter to control pulse generator 202 to deliver one or more pacing pulses in accordance with the determined control parameter. For example, the pulse width or other aspect of the trigger signal may be determined by control module 206 and used to set the pulse width (or another aspect) of the pacing pulse.

Receiver 212 receives trigger signals through coupling member 180. Receiver 212 includes one or more receiving transducers, which may be mounted directly along an inner surface of coupling member 180, e.g., for receiving sound waves or light. The trigger signal causes a receiving transducer to produce a voltage signal that is passed to a comparator included in receiver 212 (or control module 206) for comparison to a trigger signal detection threshold. If the voltage signal produced by the receiving transducer is greater than the detection threshold, a trigger detect signal 216 is passed to control module 206, or directly to pulse generator 202, to cause pacing pulse delivery.

The receiver 212 is configured to detect only the emitting device-generated trigger signal in some embodiments. For example, receiver 212 may be "tuned" to detect an acoustical or optical signal of a particular signal frequency or bandwidth that is outside a normal physiological range of acoustical or optical signal sensing. In some examples, receiver 212 is not configured to sense and process any physiological acoustical signals or optical signals for determining a physiological event, condition or state.

Control module 206 controls pulse generator 202 to deliver a pacing pulse according to therapy delivery control parameters such as pulse amplitude, pulse width, pulse number, etc., which may be stored in memory 210. In some examples, pulse generator 202 is enabled to deliver a pacing pulse immediately upon receiving a trigger detect signal 216, either directly from receiver 212 or via control module 206. Alternatively, the pacing pulse may be delivered after a predetermined time delay.

Receiver 212 may include multiple receiving transducers for sensing the trigger signal. The voltage signal produced by multiple transducers may be summed, for example, for comparison to a trigger signal detection threshold. In some embodiments, multiple receiving transducers may be included that are responsive to different frequency bandwidths. Providing detection of different signal frequencies may enable different trigger signals to be transmitted for causing therapy delivery device 100 to perform different pacing functions and/or improve trigger signal detection.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries.

Circuitry represented by the block diagram shown in FIG. 4 may include any discrete and/or integrated electronic circuit components that implement analog and/or digital circuits capable of producing the functions attributed to therapy delivery device 100 herein. The functions attributed to therapy delivery device 100 herein may be embodied as one or more processors, hardware, firmware, software, or any combination thereof. Control module 206 may include any one or more of a microprocessor, a controller, a digital signal processor (DSP), an application specific integrated circuit (ASIC), a field-programmable gate array (FPGA), state machine, or equivalent discrete or integrated logic circuitry. Depiction of different features of therapy delivery device 100 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components, which may include combinational or sequential logic circuits, state machines, memory devices, etc.

Memory 210 may include computer-readable instructions that, when executed by control module 206, cause control module 206 to perform various functions attributed throughout this disclosure to therapy delivery device 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores intervals, counters, or other data used by control module 206 to control the delivery of pacing pulses by pulse generator 202 in response to detection of a trigger signal received by receiver 212.

Figure 5:
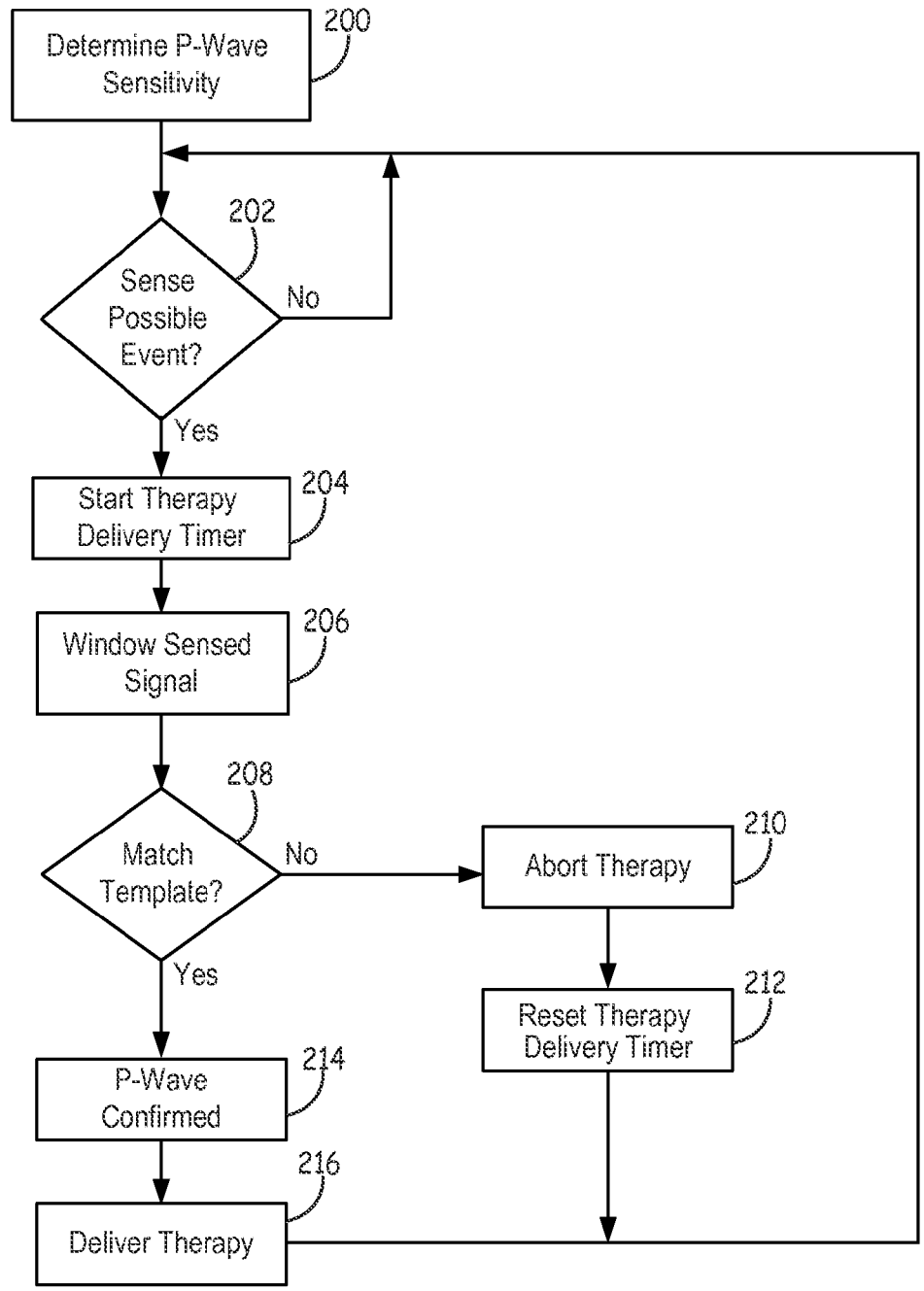
FIG. 5 is a flowchart of a method for sensing an atrial event for timing of delivery of therapy in an implantable medical device system, according to an embodiment of the present disclosure.

FIG. 5 is a flowchart of a method for sensing an atrial event for timing of delivery of therapy in an implantable medical device system, according to an embodiment of the present disclosure. According to one embodiment, in order to determine whether a P-wave event is occurring, a template generated from average P-wave morphologies determined from a predetermined patient population may be utilized, using known template generation schemes. In another embodiment, since P-wave morphologies may vary from patient to patient, a P-wave template may be generated either at implant by the implanting physician based on determined P-wave morphologies of the patient and using known template generation schemes, or may be automatically generated by the implanted device.

Figure 6:
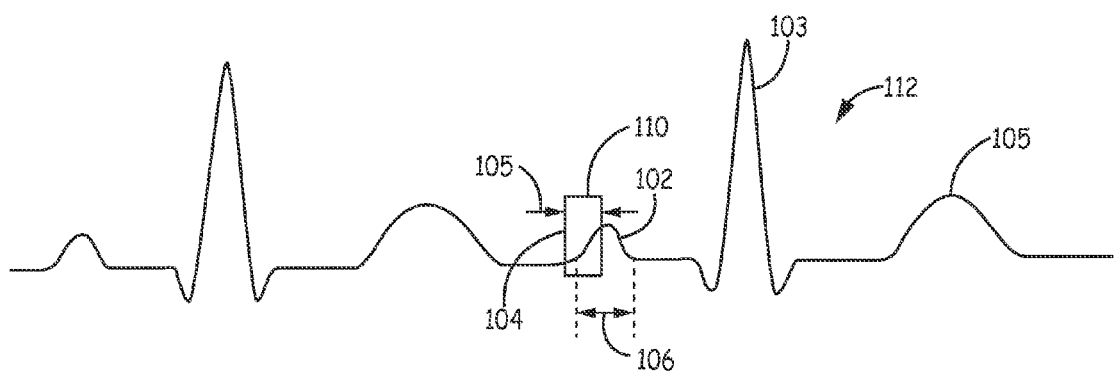
FIG. 6 is a schematic diagram of sensing of an atrial event for timing of delivery of therapy in an implantable medical device system, according to an embodiment of the present disclosure.

FIG. 6 is a schematic diagram of sensing of an atrial event for timing of delivery of therapy in an implantable medical device system, according to an embodiment of the present disclosure. As illustrated in FIG. 6, the sensing device 14 sensing a cardiac signal 112 to monitor the signal 112, including a identifying a P-wave 102, an R-wave 103, and a T-wave 105, and determine the occurrence of a cardiac event. During delivery of cardiac resynchronization pacing therapy, in order to ensure that the ventricular pacing stimulus is delivered in synchrony with atrial activity to maintain atrioventricular synchrony, and that the delivered pacing therapy results in an appropriate evoked response from the ventricle, delivery of the pacing therapy is typically timed off of a sensed P-wave 102. During delivery of the cardiac resynchronization pacing therapy, a sensed atrioventricular (SAV) delay, which is a time period between a sensed atrial event and a paced ventricular event, is typically nominally set as 100 ms, so that the amount of time in which the confirmation of a P-wave 102 must occur in order to time the delivery of the pacing therapy must occur within 100 ms of sensing the P-wave 102. However, the typical duration of a P-wave exceeds 100 ms, making timing of the delivery of therapy problematic. Therefore, as illustrated in FIG. 6, according to an embodiment of the present disclosure, in order to reduce the time required to confirm the occurrence of a P-wave 102, a P-wave template 110 is generated having a P-wave window 104 whose length 105 is less than a width 106 of a P-wave 102 of the sensed cardiac signal 112. For example, the length 105 of the P-wave window 104 may be set as a predetermined percentage of width 106 of the P-wave 102, such as 50%, for example, that still enables the essential morphologic characteristics of the P-wave 102 to be identified, depending on specific patient tendencies. It is understood that, while the SAV delay is nominally set as 100 ms, other values may be utilized, depending on certain patient requirements, and may be within a range of approximately 80-300 ms. In addition, the P-wave template may be periodically updated to address changes in P-wave morphology/features over time.

As illustrated in FIGS. 5 and 6, as described above, the P-wave template 110 is generated corresponding to a desired P-wave sensitivity, such as 50% for example, either during implant by a physician or post-implant by the implanted device, Block 200. The sensing device 14 senses the cardiac signal 112 of the patient and, based on the sensed cardiac signal 112, determines whether a possible P-wave event, i.e., a cardiac event not yet confirmed as a P-wave event, is sensed, Block 202. The basis of determination of a possible P-wave event being sensed is based on comparing a pre-specified time-window of the signal around the time-point of sensing to a template. For the comparison, specific signal characteristics like amplitude, slope, polarity may be used or more global template matching measures like correlation coefficient or wavelet match scores may be used. For example if the correlation coefficient between the windowed signal and the P-wave template exceeds a certain amplitude threshold (e.g. 0.6, 0.65, 0.7, 0.75, 0.8, 0.85, 0.9, 0.95) the sensed signal is determined to be a possible P-wave event. In addition, according to one embodiment, the template matching may be performed using a matching scheme that is insensitive to amplitude, such as correlation waveform analysis (CWA), for example, in combination with a matching scheme that is sensitive to amplitude, such as difference of area (DOA). For example, the amplitude insensitive template matching (CWA) is applied, and if a match is determined, then the amplitude sensitive template matching scheme (DOA) is subsequently applied. If a match is again determined, using the amplitude sensitive matching scheme, the waveform is considered to match the template, and if a match is not again determined, using the amplitude sensitive matching scheme, the waveform is not considered to match the template.

Once a possible P-wave event is determined to have occurred, Yes in Block 202, the sensing device 14 initiates a ventricular pace delivery timer, Block 204, and windows the sensed signal 112 using the generated P-wave template 110, Block 206, to determine whether the cardiac signal 112 matches the P-wave template 110, Block 208. A P-wave template match may be determined, for example, by calculating a correlation coefficient based on a point-by-point comparison of the sampled signal and the stored P-wave template 110. Calculation of a correlation coefficient may be performed as generally described in U.S. Pat. No. 5,193,550 issued to Duffin, incorporated herein by reference in its entirety.

If a P-wave match is not determined to occur, No in Block 208, the possible P-wave is not confirmed as being a P-wave and delivery of the pacing therapy is aborted, Block 210. As a result, the therapy deliver timer is reset, Block 212, and the sensing device 14 waits for the next sensed possible P-wave event to occur, Block 202. If a P-wave match is determined to occur, Yes in Block 208, the possible P-wave is confirmed as being a P-wave, Block 214, and the sensing device 14 emits the trigger signal which is received by the therapy delivery device 100, which then initiates delivery of the pacing therapy, Block 216, utilizing the confirmed sensed P-wave 102 for timing of the delivered therapy.

Figure 7:
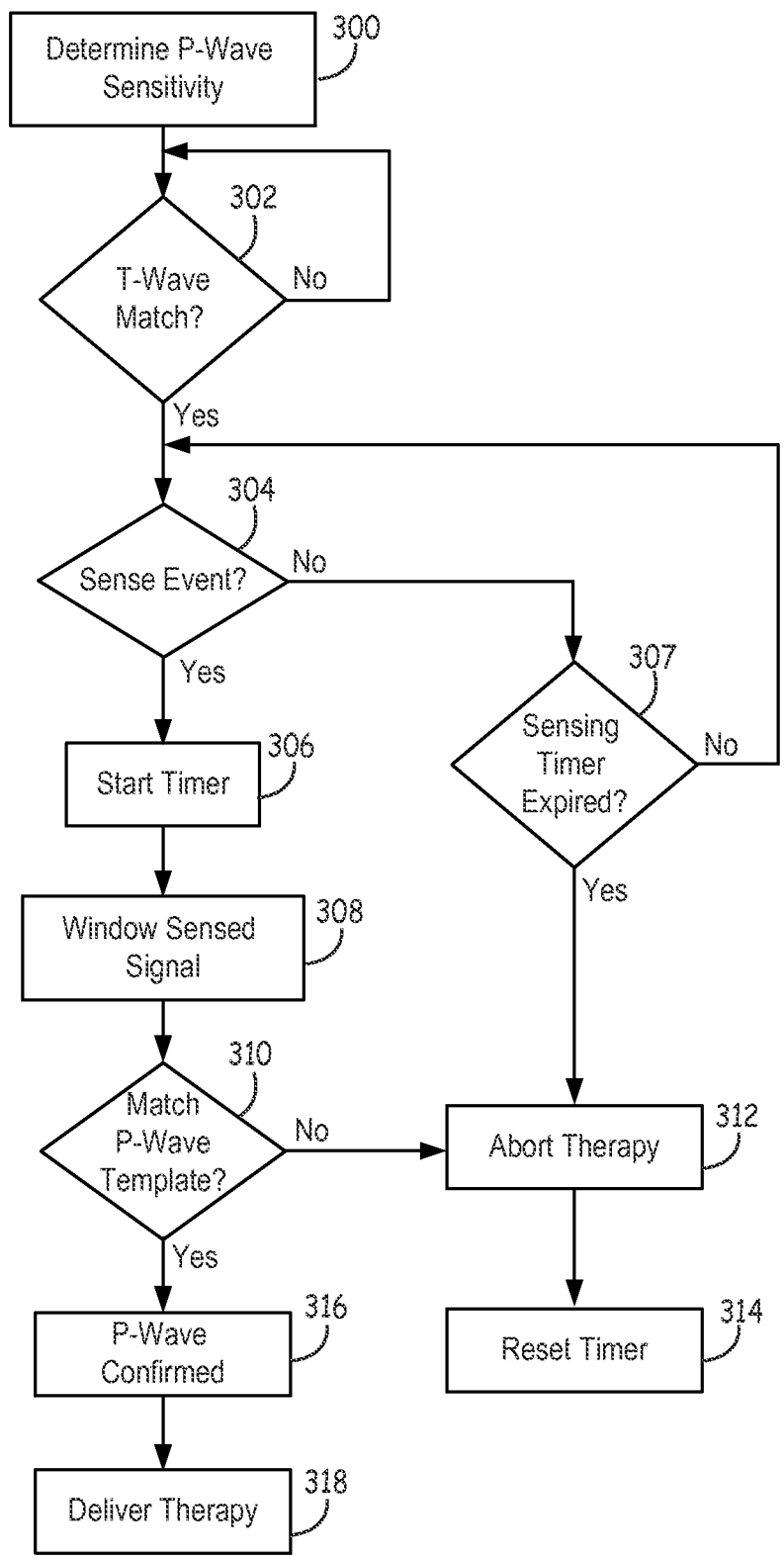
FIG. 7 is a flowchart of a method for sensing of an atrial event for timing of delivery of therapy in an implantable medical device system, according to an embodiment of the present disclosure.

FIG. 7 is a flowchart of a method for sensing of an atrial event for timing of delivery of therapy in an implantable medical device system, according to an embodiment of the present disclosure. In some circumstances, a T-wave portion of the cardiac signal may be mistakenly identified as being a P-wave portion of the signal. Therefore, according to another embodiment, a T-wave template, generated using known T-wave template generation schemes, is used to identify the occurrence of the T-wave. For example, as illustrated in FIG. 7, as described above, the P-wave template 110 is generated corresponding to a desired P-wave sensitivity, such as 50% for example, either during implant by a physician or post-implant by the implanted device, Block 300. The sensing device 14 senses the cardiac signal and determines whether a T-wave match occurs, Block 302, using a known T-wave template matching scheme. For example, a T-wave template match may be determined, for example, by calculating a correlation coefficient based on a point-by-point comparison of the sampled signal and the stored T-wave template. Other known T-wave matching schemes may be utilized, such as described in U.S. Pat. No. 7,831,304 to Cao, et al., for example, or in U.S. Patent Publication No 2006/0116592 to Zhou et al., both incorporated herein by reference in their entireties.

Once a T-wave match is determined to occur, Yes in Block 302, the sensing device 14 determines, based on the sensed cardiac signal 112, whether a possible P-wave event is sensed, Block 304, as described above. The sensing device 14 continues to determine whether a possible P-wave is sensed, Block 304 for a predetermined period of time after sensing of the T-wave, such as between 200 and 500 ms, for example. Therefore, during the determination of whether a possible P-wave event is present in Block 304, the device monitors whether a determination is made as to whether a predetermined time period has expired, Block 307, so that if the device 14 is unable to determine that a possible P-wave event has been sensed after sensing of the T-wave within the predetermined time period, Yes in Block 307, the possible P-wave is not confirmed as being a P-wave and delivery of the pacing therapy is aborted, Block 312. As a result, the therapy deliver timer is reset, Block 314, and the sensing device 14 waits for the next T-wave to be sensed, Block 302. Once the sensing device 14 determines a possible P-wave event has occurred, Yes in Block 304, the sensing device 14 initiates a ventricular pace delivery timer, Block 306, and windows the sensed cardiac signal 112 using the generated P-wave template 110, Block 308, to determine whether the signal matches the P-wave template 110, Block 310, as described above.

If a P-wave match is not determined to occur, No in Block 310, the possible P-wave is not confirmed as being a P-wave and delivery of the pacing therapy is aborted, Block 312. As a result, the therapy deliver timer is reset, Block 314, and the sensing device 14 waits for the next T-wave to be sensed, Block 302. If a P-wave match is determined to occur, Yes in Block 310, the possible P-wave is confirmed as being a P-wave, Block 316, and the sensing device 14 emits the trigger signal to the therapy delivery device 100, which then initiate delivery of the pacing therapy via the therapy delivery device 100, Block 318, utilizing the confirmed sensed P-wave for timing of the delivered therapy.

The techniques described in this disclosure, including those attributed to the IMD, the programmer, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A medical device system for controlling delivery of therapeutic stimulation pulses, the medical device system comprising:
   a sensing device configured to:
      sense a cardiac signal of a patient; and
      emit a trigger signal in response to the sensed cardiac signal;
   a therapy delivery device configured to:
      receive the trigger signal; and
      deliver therapy to the patient in response to the emitted trigger signal; and
   a processor positioned within the sensing device, the processor being configured to:
      determine whether the sensed cardiac signal exceeds a P-wave candidate threshold;
      compare, in response to a determination that the sensed cardiac signal exceeds the P-wave candidate threshold, a portion of the sensed cardiac signal to a P-wave template, the P-wave template comprising a sensing window having a length less than a width of a P-wave with a predetermined P-wave morphology, the sensing window corresponding to a time window that ends prior to an end of the P-wave with the predetermined P-wave morphology;
      confirm an occurrence of a P-wave in the sensed cardiac signal in response to the comparison between the portion of the sensed cardiac signal and the P-wave template;
      generate, in response to the occurrence of the P-wave in the sensed cardiac signal being confirmed, the trigger signal emitted by the sensing device; and
      inhibit delivery of the trigger signal in response to the occurrence of the P-wave in the sensed cardiac signal not being confirmed.

2. The medical device system of claim 1, wherein the sensing device comprises a subcutaneous device capable of being implanted subcutaneously within a patient and the therapy delivery device comprises a transcatheter intracardiac pacemaker adapted for implantation wholly within a heart chamber.

3. The medical device system of claim 1, wherein the sensing device comprises subcutaneously implanted electrodes to sense the cardiac signal.

4. The medical device system of claim 1, wherein the sensing device comprises a subcutaneously implanted leadless device.

5. The medical device system of claim 1, wherein the length of the sensing window of the P-wave template corresponds to a predetermined percentage of the width of the P-wave with the predetermined P-wave morphology.

6. The medical device system of claim 5, wherein the predetermined percentage is fifty percent (50%).

7. The medical device system of claim 1, wherein the therapeutic stimulation pulses comprise cardiac resynchronization therapy pacing pulses.

8. The medical device system of claim 1, wherein the P-wave candidate threshold comprises at least one of an amplitude or a slope.

9. A medical device system for controlling delivery of therapeutic stimulation pulses, the medical device system comprising:
   a sensing device configured to:
      sense a cardiac signal of a patient; and
      emit a trigger signal in response to the sensed cardiac signal;
   a therapy delivery device configured to:
      receive the trigger signal; and
      deliver therapy to the patient in response to the emitted trigger signal; and
   a processor positioned within the sensing device, the processor being configured to:
      determine whether the cardiac signal comprises a T-wave;
      determine, in response to a determination that the cardiac signal comprises a T-wave, whether the sensed cardiac signal exceeds a P-wave candidate threshold;
      compare, in response to a determination that the sensed cardiac signal exceeds the P-wave candidate threshold, a portion of the sensed cardiac signal to a P-wave template, the P-wave template comprising a sensing window having a length less than a width of a P-wave with a predetermined P-wave morphology, the sensing window corresponding to a time window that ends prior to an end of the P-wave with the predetermined P-wave morphology;
      confirm an occurrence of a P-wave in the sensed cardiac signal in response to the comparison between the portion of the sensed cardiac signal and the P-wave template;
      generate, in response to the occurrence of a P-wave in the sensed cardiac signal being confirmed, the trigger signal emitted by the sensing device; and
      inhibit delivery of the trigger signal in response to one of the T-wave not occurring and the occurrence of the P-wave in the sensed cardiac signal not being confirmed.

10. The medical device system of claim 9, wherein the sensing device comprises a subcutaneous device capable of being implanted subcutaneously within a patient and the therapy delivery device comprises a transcatheter intracardiac pacemaker adapted for implantation wholly within a heart chamber.

11. The medical device system of claim 9, wherein the sensing device comprises subcutaneously implanted electrodes to sense the cardiac signal.

12. The medical device system of claim 9, wherein the sensing device comprises a subcutaneously implanted leadless device.

13. The medical device system of claim 9, wherein the length of the sensing window of the P-wave template corresponds to a predetermined percentage of the width of the P-wave with the predetermined P-wave morphology.

14. The medical device system of claim 13, wherein the predetermined percentage is fifty percent (50%).

15. The medical device system of claim 9, wherein the therapeutic stimulation pulses comprise cardiac resynchronization therapy pacing pulses.

16. The medical device system of claim 9, wherein the P-wave candidate threshold comprises at least one of an amplitude or a slope.

17. A method of delivering therapeutic stimulation pulses, the method comprising:
sensing a cardiac signal of a patient;
receiving a trigger signal;
delivering therapy to the patient via a therapy delivery device in response to the emitted trigger signal;
determining whether the sensed cardiac signal exceeds a P-wave candidate threshold;
comparing, in response to determining that the sensed cardiac signal exceeds the P-wave candidate threshold, a portion of the sensed cardiac signal to a P-wave template, the P-wave template comprising a sensing window having a length less than a width of a P-wave with a predetermined P-wave morphology, the sensing window corresponding to a time window that ends prior to an end of the P-wave with the predetermined P-wave morphology;
confirming an occurrence of a P-wave in the sensed cardiac signal in response to the comparison between the portion of the sensed cardiac signal and the P-wave template;
generating the trigger signal in response to the occurrence of the P-wave in the sensed cardiac signal being confirmed; and
inhibiting delivery of the trigger signal in response to the occurrence of the P-wave in the sensed cardiac signal not being confirmed.

18. The method of claim 17, wherein the sensing device comprises a subcutaneous device capable of being implanted subcutaneously within a patient and the therapy delivery device comprises a transcatheter intracardiac pacemaker adapted for implantation wholly within a heart chamber.

19. The method of claim 17, wherein the sensing device comprises subcutaneously implanted electrodes to sense the cardiac signal.

20. The method of claim 17, wherein the sensing device comprises a subcutaneously implanted leadless device.

21. The method of claim 17, wherein the length of the sensing window of the P-wave template corresponds to a predetermined percentage of the width of the P-wave with the predetermined P-wave morphology.

22. The method of claim 21, wherein the predetermined percentage is fifty percent (50%).

23. The method of claim 17, wherein the therapeutic stimulation pulses comprise cardiac resynchronization therapy pacing pulses.

24. The method of claim 17, wherein the P-wave candidate threshold comprises at least one of an amplitude or a slope.

25. A method of delivering therapeutic stimulation pulses, the method comprising:
sensing a cardiac signal of a patient;
receiving a trigger signal;
delivering therapy to the patient via a therapy delivery device in response to the emitted trigger signal;
determining whether the cardiac signal comprises a T-wave;
determining, in response to a T-wave occurring, whether the sensed cardiac signal exceeds a P-wave candidate threshold;
comparing, in response to determining that the sensed cardiac signal exceeds the P-wave candidate threshold, a portion of the sensed cardiac signal to a P-wave template, the P-wave template comprising a sensing window having a length less than a width of a P-wave with a predetermined P-wave morphology, the sensing window corresponding to a time window that ends prior to an end of the P-wave with the predetermined P-wave morphology;
confirming an occurrence of a P-wave in the sensed cardiac signal in response to the comparison between the portion of the sensed cardiac signal and the P-wave template;
generating the trigger signal in response to the occurrence of the P-wave in the sensed cardiac signal being confirmed; and
inhibiting delivery of the trigger signal in response to one of the T-wave not occurring and the occurrence of the P-wave in the sensed cardiac signal not being confirmed.

26. The method of claim 25, wherein the sensing device comprises a subcutaneous device capable of being implanted subcutaneously within a patient and the therapy delivery device comprises a transcatheter intracardiac pacemaker adapted for implantation wholly within a heart chamber.

27. The method of claim 25, wherein the sensing device comprises subcutaneously implanted electrodes to sense the cardiac signal.

28. The method of claim 25, wherein the sensing device comprises a subcutaneously implanted leadless device.

29. The method of claim 25, wherein the length of the sensing window of the P-wave template corresponds to a predetermined percentage of the width of the P-wave with the predetermined P-wave morphology.

30. The method of claim 29, wherein the predetermined percentage is fifty percent (50%).

31. The method of claim 25, wherein the therapeutic stimulation pulses comprise cardiac resynchronization therapy pacing pulses.

32. The method of claim 25, wherein the possible P-wave threshold comprises at least one of an amplitude or a slope.

33. A medical device for controlling delivery of therapeutic stimulation pulses, the medical device comprising:
a subcutaneous sensing device comprising subcutaneously implanted electrodes configured to sense a cardiac signal of a patient;
an emitting device configured to emit a trigger signal to deliver the therapeutic stimulation pulses in response to the sensed cardiac signal; and
a processor positioned within the subcutaneous sensing device, the processor configured to:
determine whether the sensed cardiac signal exceeds a P-wave candidate threshold,
compare, in response to a determination that the sensed cardiac signal exceeds the P-wave candidate threshold, a portion of the sensed cardiac signal to a P-wave template, the P-wave template comprising a sensing window having a length less than a width of a P-wave with a predetermined P-wave morphology, the sensing window corresponding to a time window that ends prior to an end of the P-wave with the predetermined P-wave morphology;
confirm an occurrence of a P-wave in the sensed cardiac signal in response to the comparison between the portion of the sensed cardiac signal and the P-wave template;
generate, in response to the occurrence of the P-wave in the sensed cardiac signal being confirmed, the trigger signal emitted by the emitting device; and
inhibit delivery of the trigger signal in response to the occurrence of the P-wave in the sensed cardiac signal not being confirmed.

34. The medical device of claim 33, wherein the length of the sensing window of the P-wave template corresponds to a predetermined percentage of the width of the P-wave with the predetermined P-wave morphology.

35. The medical device of claim 34, wherein the predetermined percentage is fifty percent (50%).

36. The medical device of claim 33, wherein the therapeutic stimulation pulses comprise cardiac resynchronization therapy pacing pulses.

37. The medical device of claim 33, wherein the P-wave candidate threshold comprises at least one of an amplitude or a slope.

\* \* \* \* \*